(12) United States Patent
Gross et al.

(10) Patent No.: US 11,397,282 B1
(45) Date of Patent: Jul. 26, 2022

(54) INFRARED-TRANSPARENT POLYMER OPTICS AND METHODS OF MAKING AND USING THE SAME

(71) Applicant: HRL Laboratories, LLC, Malibu, CA (US)

(72) Inventors: Adam F. Gross, Santa Monica, CA (US); Ashley M. Dustin, Los Angeles, CA (US); Andrew P. Nowak, Los Angeles, CA (US); April R. Rodriguez, Santa Monica, CA (US); Rajesh D. Rajavel, Oak Park, CA (US); Jacob M. Hundley, Thousand Oaks, CA (US)

(73) Assignee: HRL Laboratories, LLC, Malibu, CA (US)

( * ) Notice: Subject to any disclaimer, the term of this patent is extended or adjusted under 35 U.S.C. 154(b) by 649 days.

(21) Appl. No.: 16/427,290

(22) Filed: May 30, 2019

Related U.S. Application Data

(60) Provisional application No. 62/691,707, filed on Jun. 29, 2018, provisional application No. 62/691,710, filed on Jun. 29, 2018.

(51) Int. Cl.
| | | |
|---|---|---|
| *G02B 1/04* | (2006.01) | |
| *C08G 79/025* | (2016.01) | |
| *C08J 3/24* | (2006.01) | |
| *C08K 3/013* | (2018.01) | |
| *C08K 7/18* | (2006.01) | |
| *G02B 1/14* | (2015.01) | |
| *G02B 1/11* | (2015.01) | |
| *G02B 1/18* | (2015.01) | |
| *C08K 7/04* | (2006.01) | |

(52) U.S. Cl.
CPC ............ *G02B 1/04* (2013.01); *C08G 79/025* (2013.01); *C08J 3/24* (2013.01); *C08K 3/013* (2018.01); *C08K 7/04* (2013.01); *C08K 7/18* (2013.01); *G02B 1/11* (2013.01); *G02B 1/14* (2015.01); *G02B 1/18* (2015.01); *C08K 2201/005* (2013.01); *C08K 2201/011* (2013.01)

(58) Field of Classification Search
CPC ............ G02B 1/04; G02B 1/11; G02B 1/14; G02B 1/18; C08K 3/013; C08K 7/04; C08K 7/18; C08K 2201/005; C08K 2201/011; C08G 79/025; C08J 3/24
See application file for complete search history.

(56) References Cited

U.S. PATENT DOCUMENTS

| | | | |
|---|---|---|---|
| 3,164,556 A | 1/1965 | Apley et al. | |
| 3,364,189 A | 1/1968 | Allcock et al. | |
| 3,370,020 A | 2/1968 | Allcock et al. | |
| 3,443,913 A | 5/1969 | Bieniek et al. | |
| 4,237,263 A | 12/1980 | Allcock et al. | |
| 4,988,791 A | 1/1991 | Maruyama et al. | |
| 5,464,932 A | 11/1995 | Allcock et al. | |
| 5,546,493 A | 8/1996 | Noguchi et al. | |
| 5,562,909 A | 10/1996 | Allcock et al. | |
| 5,633,077 A | 5/1997 | Olinger | |
| 5,747,604 A | 5/1998 | Allcock et al. | |
| 7,258,923 B2 | 8/2007 | van den Bogerd | |
| 7,915,441 B2 | 3/2011 | Fushimi | |
| 8,093,559 B1 | 1/2012 | Rajavel | |
| 2002/0176158 A1* | 11/2002 | Minami | .............. G02B 1/14 359/356 |
| 2017/0022385 A1 | 1/2017 | Nowak et al. | |

FOREIGN PATENT DOCUMENTS

| | | |
|---|---|---|
| EP | 2883919 B1 | 6/2015 |
| EP | 2764320 B1 | 2/2018 |

OTHER PUBLICATIONS

We et al., "A rapid and efficient strategy for preparation of super-hydrophobic surface with cross-linked cyclotriphosphazene/6F-bisphenol A copolymer microspheres", Chem. Commun., 2010, 46, 487-489.
Tsilingiris, "Comparative evaluation of the infrared transmission of polymer films", Energy Conversion and Management 44 (2003) 2839-2856.
Allcock, "The Synthesis of Functional Polyphosphazenes and their Surfaces", Appl. Organom et al. Chem. 12, 659-666 (1998).
Non-Final Office Action, U.S. Appl. No. 16/427,265, dated Apr. 6, 2022.

* cited by examiner

*Primary Examiner* — Edward J Cain
(74) *Attorney, Agent, or Firm* — O'Connor & Company; Ryan P. O'Connor

(57) ABSTRACT

Infrared-transparent and damage-resistant polymer optics with LWIR and/or MWIR transparency are provided. Some variations provide an optic containing at least 50 wt % of an infrared-transparent polymer, wherein the infrared-transparent polymer has a carbon-free polymer backbone, wherein the optic is characterized by at least 80% average transmission of radiation over a wavenumber band with cumulative wavenumber width of at least 1000 cm$^{-1}$ contained within wavelengths from 3.1 μm to 5 μm and/or from 8.1 μm to 12 μm, and wherein the average transmission is defined as the percentage ratio of radiation intensity through an optic thickness of 25 microns divided by incident radiation intensity. Many polymer compositions and pendant groups are disclosed for use in the polymer optics.

30 Claims, 6 Drawing Sheets

INFRARED-TRANSPARENT POLYMER OPTICS AND METHODS OF MAKING AND USING THE SAME

PRIORITY DATA

This patent application is a non-provisional application claiming priority to U.S. Provisional Patent App. No. 62/691,707, filed on Jun. 29, 2018, and to U.S. Provisional Patent App. No. 62/691,710, filed on Jun. 29, 2018, each of which is hereby incorporated by reference herein.

FIELD OF THE INVENTION

The present invention generally relates to infrared-transparent optics, and in particular infrared-transparent polymer optics.

BACKGROUND OF THE INVENTION

Infrared radiation is emitted or absorbed by molecules when they change their rotational and vibrational movements. Infrared radiation excites vibrational modes in a molecule through a change in the dipole moment, making infrared a useful frequency range for study of energy states for molecules. Infrared spectroscopy examines absorption and transmission of photons in the infrared range.

Infrared radiation is used in industrial, scientific, military, law enforcement, and medical applications. Applications include target acquisition, surveillance, night vision, homing, tracking, thermal efficiency analysis, environmental monitoring, industrial facility inspections, remote temperature sensing, short-range wireless communication, and weather forecasting. Night-vision devices using active near-infrared illumination allow people or animals to be observed without the observer being detected or with additional illumination at night. Infrared astronomy uses sensor-equipped telescopes to penetrate dusty regions of space such as molecular clouds, detect objects such as planets, and view highly red-shifted objects from the early days of the universe. Infrared thermal-imaging cameras are used to detect heat loss in insulated systems, observe changing blood flow in the skin, and detect overheating of electrical apparatus.

The medium wavelength infrared (MWIR) and the long wavelength infrared (LWIR) bands find applications in infrared thermography for military or civil applications, e.g. target signature identification, surveillance, and non-destructive evaluation. The 3-5 micron MWIR band may be preferred when inspecting high-temperature objects, and the 8-12 micron LWIR band may be preferred when working with near-room-temperature objects. Other criteria for band selection include the operating distance, indoor versus outdoor operation, temperature, and emissivity of the bodies of interest.

Modern infrared cameras operate over multiple bands in both the MWIR and LWIR spectrums. In order to function successfully, the camera's detector surface is usually enclosed in an IR-transparent window or domed enclosure. When used in service on an automotive or aerospace vehicle, the enclosure must not only be IR-transparent but also able to withstand considerable environmental exposure in the form of temperature extremes along with high-speed erosion causes including wind, rain, ice, dust, and dirt. Such conditions will rapidly degrade soft, non-durable transmission windows through erosion and surface etching.

Other applications utilizing LWIR optics require environmental durability and mechanical strength, in addition to infrared optical transparency. That is, the materials must simultaneously serve as optical and structural materials. The dual requirements make this a particularly difficult materials problem. There is a need in the art to reduce the cost and increase the durability of materials that function in the MWIR and LWIR bands. Tough, low-cost IR windows and lenses are particularly sought.

Semiconductors and oxides are known IR-transparent materials but suffer from various deficiencies, such as being prone to environmental damage during use.

Environmental damage can be caused by cracking or scratching, for example. The resistance to cracking can be described by toughness, while the resistance to scratching can be described by hardness. Toughness itself can be characterized as the work of fracture, which is the energy required to propagate a crack in the material.

Aluminum oxynitride (AlON) is a ceramic that is IR-transparent at wavelengths from 0.25 µm to 4.5 µm. It has a density of 3.7 g/cm$^3$ and an index of refraction of 1.8. AlON is damage-resistant as well as thermally stable to temperatures of 1900° C. However, AlON is a very expensive material.

Sapphire is IR-transparent at wavelengths from 0.15 µm to 5 µm. It has a density of 4 g/cm$^3$ and an index of refraction of 3.9. Sapphire is damage-resistant as well as thermally stable to temperatures of 1800° C. However, sapphire is a precious gemstone and is very expensive.

Germanium (Ge) is IR-transparent at wavelengths from 3 µm to 12 µm. It has a density of 2.3 g/cm$^3$ and an index of refraction of 1.7. Germanium is not damage-resistant, is not thermally stable above 200° C. and starts to lose IR transparency above 100° C., and does not scale-up well. Germanium is a very expensive material.

Zinc sulfide (ZnS) and zinc selenide (ZnSe) are IR-transparent at wavelengths from 3 µm to 12 µm. ZnS has a density of 4.1 g/cm$^3$ and an index of refraction of 2.2, while ZnSe has a density of 5.3 g/cm$^3$ and an index of refraction of 2.4. These materials are only somewhat damage-resistant, and they do not scale-up well. Both ZnS and ZnSe are extremely expensive and are not stable above 200° C.

Advanced chalcogenide alloys (e.g., $Ge_{28}Sb_{12}Se_{60}$ or $As_{40}Se_{60}$) also suffer from low work of fracture and do not scale-up well.

The aforementioned metal and ceramic materials are not economic for many applications. In addition to that, semiconductor or oxide inorganic windows have low damage resistance due to low work of fracture.

There is a desire for IR-transparent materials that are in the form of polymers, which are generally much less expensive.

Polyethylene is a polymer that is IR-transparent at wavelengths from 4 µm to 6.5 µm and from 7.5 µm to 12 µm. Polyethylene has a density of about 1 g/cm$^3$ and an index of refraction of 1.53. Although polyethylene is a low-cost material, it is not damage-resistant which limits its applications for IR-transparent materials. Polyethylene cannot normally be crosslinked to make it a hard (thermoset) polymer. The polymer is thus soft and easily scratched, resulting in a material that will scatter light when damaged.

Polytetrafluoroethylene (PTFE) is a polymer that is IR-transparent at wavelengths from about 3 µm to 7.5 µm and from about 9 µm to about 15 µm. PTFE has a density of about 2.2 g/cm$^3$ and an index of refraction of about 1.4. Although PTFE is a relatively low-cost material, it is not damage-resistant which limits its applications for IR-transparent materials. PTFE cannot normally be crosslinked to make it a hard (thermoset) polymer. The polymer is thus soft, resulting in a material that will scatter light when damaged.

Cyclic olefin copolymers, even when they meet the dual requirements of good hardness and work of fracture, typically have narrow IR transparency bands (e.g., from about 3 µm to about 4 µm).

The damage resistance that is especially desired is a combination of work of fracture and hardness, which is difficult to achieve. For example, AlON, sapphire, Ge, ZnS, and ZnSe all have good hardness but low work of fracture. Polyethylene, PTFE, and similar polymers have good work of fracture but low hardness. See, for example, FIG. 6.

What is desired is a low-cost, damage-resistant, infrared-transparent polymer optic with LWIR and/or MWIR transparency. The IR-transparent polymer preferably has a work of fracture greater than that of the ceramic materials discussed above and a hardness greater than that of polycarbonate. Polycarbonate is not IR-transparent but is used in visible windows and lenses that require hardness, and thus is a good material for comparison.

SUMMARY OF THE INVENTION

The present invention addresses the aforementioned needs in the art, as will now be summarized and then further described in detail below.

Some variations provide an optic containing at least 50 wt % of an infrared-transparent polymer, wherein the infrared-transparent polymer has a carbon-free polymer backbone, wherein the optic is characterized by at least 80% average transmission of radiation over a wavenumber band with cumulative wavenumber width of at least 1000 cm$^{-1}$ contained within wavelengths from 3.1 µm to 5 µm and/or from 8.1 µm to 12 µm, and wherein the average transmission is defined as the ratio (expressed as a percentage) of radiation intensity through an optic thickness of 25 microns divided by incident radiation intensity.

In some embodiments, the cumulative wavenumber width is at least 1500 cm$^{-1}$, or at least 2000 cm$^{-1}$, contained within wavelengths from 3.1 µm to 5 µm and/or from 8.1 µm to 12 µm.

In some embodiments, the carbon-free polymer backbone contains a plurality of polymer repeat units of the form

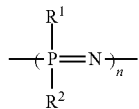

wherein $R^1$ is selected from the group consisting of halogens, alkyls, hydroxyl, amino, urea, thiol, thioether, amino alkyls, carboxylates, metals, metal-containing groups, and derivatives, deuterated forms, or combinations thereof;

wherein $R^2$ is selected from the group consisting of halogens, alkyls, hydroxyl, amino, urea, thiol, thioether, amino alkyls, carboxylates, metals, metal-containing groups, and derivatives, deuterated forms, or combinations thereof;

wherein n is selected from 2 to about 10,000; and
wherein the carbon-free polymer backbone is linear, cyclic, branched, or a combination thereof.

In some embodiments, Ie and $R^2$ are independently selected from the group consisting of Cl, $CH_3$, $NH_2$, $NH(CH_2)_3CH_3$, $NH(CO)NH_2$, COOH, O(CO)OH, OTi(OH)$_3$, SH, and derivatives, deuterated forms, or combinations thereof.

In some embodiments, the carbon-free polymer backbone contains at least one polymer repeat unit of the form

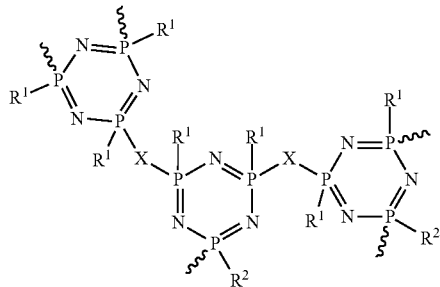

wherein $R^1$ is selected from the group consisting of halogens, alkyls, hydroxyl, amino, urea, thiol, thioether, amino alkyls, carboxylates, metals, metal-containing groups, and derivatives, deuterated forms, or combinations thereof;

wherein $R^2$ is selected from the group consisting of halogens, alkyls, hydroxyl, amino, urea, thiol, thioether, amino alkyls, carboxylates, metals, metal-containing groups, and derivatives, deuterated forms, or combinations thereof; and wherein X is a crosslinking group, and optionally wherein X is $R^1$ or $R^2$.

The carbon-free polymer backbone may be crosslinked with sulfur and/or with disulfide (S—S) bonds. The carbon-free polymer backbone may be crosslinked with dithiols. Alternatively, or additionally, the carbon-free polymer backbone may be crosslinked with $CH_2$, NH, NH(CO)NH, COO-$M^{2+}$-OOC, O(CO)O, O—Ti(OH)$_2$—O, or a combination thereof.

In some embodiments, the infrared-transparent polymer is a thermoset polymer. The infrared-transparent polymer may be characterized by a density from about 1.2 g/cm$^3$ to about 1.9 g/cm$^3$, for example. The infrared-transparent polymer may be characterized by an index of refraction from about 1.3 to about 1.9, for example.

In some variations, the optic includes, or is disposed in physical contact with, an anti-scratch layer, an anti-abrasion layer, an anti-reflection layer, or a combination thereof.

In some embodiments, the optic includes an anti-scratch layer that contains diamond, diamond-like carbon, sapphire, silicon, ZnS, or a combination thereof, for example.

In some embodiments, the optic includes an anti-reflection layer in the form of a stack of films that provides anti-reflection properties.

In some embodiments, the optic includes an anti-rain erosion layer. The anti-rain erosion layer may contain an elastomeric material, such as (but not limited to) a polyphosphazene-based polymer or copolymer. The elastomeric material may be covalently or physically bonded to the optic. In certain embodiments, the elastomeric material has a storage modulus from about 1 MPa to about 500 MPa, and a minimum elongation of 100%.

In some embodiments, the optic contains toughening filler particles, such as (but not limited to) toughening filler particles selected from the group consisting of Ge, CaF$_2$, NaCl, KCl, KBr, diamond, Si, CsI, MgO, MgF$_2$, LiF, NaF, BaF$_2$, ZnS, ZnSe, PbS, Pb Se, PbF$_2$, LiYF$_4$, NaYF$_4$, ThBrI, ThBrCl, and combinations thereof. The toughening filler particles may be in the form of spheres, rods, whiskers, platelets, or a combination thereof. The toughening filler particles may have an average dimension selected from about 100 nm to about 400 µm. In certain embodiments, the toughening filler particles have an average dimension that is less than one-half of the thickness of the optic. In certain embodiments, the toughening filler particles have an average volumetric loading from about 1 vol % to about 65 vol % based on volume of the polymer plus volume of the toughening filler particles.

In some embodiments, the optic includes an anti-fouling layer on an exterior surface of the optic. The anti-fouling layer may contain a polyphosphazene-based polymer, a polyphospazene-based copolymer, or a combination thereof, for example.

In various embodiments, the optic is a single lens, a compound lens, a window, an aperture, or an array of lenses. A lens or window may be flat, curved on one axis, biaxially curved, curved in three dimensions, or a combination thereof.

DETAILED DESCRIPTION OF EMBODIMENTS OF THE INVENTION

Figure 1:
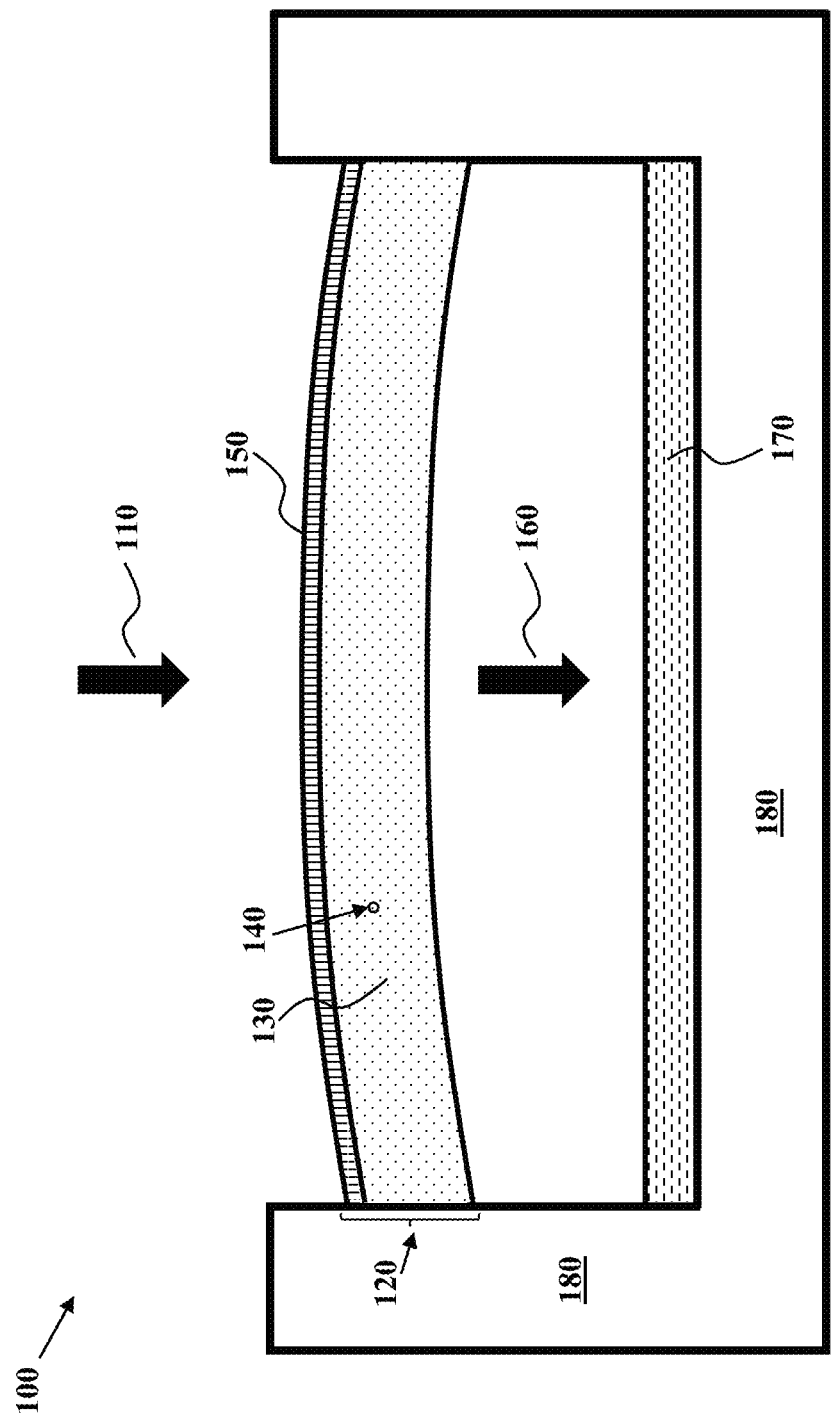
FIG. 1 depicts an exemplary optical device, in some embodiments.

The principles, materials, compositions, devices, and methods of the present invention will be described in detail by reference to various non-limiting embodiments.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with the accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms, except when used in Markush groups. Thus in some embodiments not otherwise explicitly recited, any instance of "comprising" may be replaced by "consisting of" or, alternatively, by "consisting essentially of."

The present invention provides infrared-transparent polymer optics. "Infrared-transparent polymer optics" are optics for controlling propagation of infrared (IR) light, wherein the optics contain infrared-transparent polymers. The polymers preferably have a carbon-free polymer backbone with pendant groups and/or crosslinking molecules that do not significantly absorb MWIR light, LWIR light, or both.

Conventional infrared-transparent polymers are soft and easily scratched. This low scratch resistance results in an optic that will scatter light when damaged. Typical materials, such as polyethylene and polytetrafluoroethylene, are soft because they cannot normally be crosslinked. Variations of this invention provide more-durable and more scratch-resistant polymer optics than exist today for MWIR and/or LWIR light.

Conventional semiconductor or inorganic oxide optics are highly scratch-resistant, but are difficult to scale to large areas. The polymer-based optics described in this disclosure scale easily via known polymer-processing technologies. Furthermore, conventional semiconductor or inorganic oxide optics have low work of fracture and therefore poor damage resistance. In some variations herein, crosslinked polymers provide improved hardness while retaining the work of fracture of existing thermoset polymers, while still scaling easily to $m^2$ areas.

As meant herein, an "optic" is a lens or other optical component that may be present in an optical device or another apparatus. The lens or other optical component may be a material or region that changes the behavior or properties of light (specifically, in the present disclosure, infrared light). "Optics" may refer to a singular optic or multiple optics contained in a common device. Optics may be windows for light, or lenses that affect the propagation of light, for example.

In various embodiments, optics may include, but are not limited to, plano-optics (e.g. windows, mirrors, polarizers, beam splitters, or prisms); spherical lenses (e.g. plano-concave/convex, double-concave/convex, or meniscus lenses); aspheric lenses (e.g. parabolic, hyperbolic, or hybrid lenses); achromatic lenses; assemblies (e.g. imaging lenses, beam expanders, eyepieces, or objectives); optical fibers; molded optics; optical waveguides; ring resonators; optical networks; optical interconnects; directional couplers; array waveguide grating (AWG) multi/demultiplexers; switches; tunable filters; variable optical attenuators (VOAs); amplifiers; integrated planar lightwave circuits, such as tunable optical add/drop multiplexers (OADMs), photonic crystal superprism waveguides, digital optical switches (DOSs) integrated with VOAs, or traveling-wave heterojunction phototransistors; and three-dimensionally integrated optical devices.

An "aperture" is a space through which light passes in an optical system. The aperture and focal length of an optical system determine the cone angle of a bundle of rays that come to a focus in the image plane. When the optic is an aperture, infrared-transparent polymer may form at least a portion of surrounding structures (e.g., walls) that form the aperture.

An "optical device" is a device that creates, manipulates, or measures electromagnetic radiation. An optical device may include one or more optics as listed above. Certain exemplary optical devices are night vision devices.

The infrared-transparent polymer as disclosed may be present in an MWIR and/or LWIR transparent window, an MWIR and/or LWIR lens, or an MWIR and/or LWIR optical device, for example.

In other embodiments, IR-transparent plastic panels may be placed in front of sensors to protect them after being mounted on the outside of vehicles. Some embodiments enable IR-transparent composite panels that utilize an IR-transparent fiber in the composite panel. The IR-transparent fiber would allow easy inspection for damage.

Applications include, but are not limited to, night vision systems and LiDARs that function in the MWIR and LWIR. Tougher and less breakage-prone windows and lenses are useful for highly durable IR vision systems. Infrared windows and lenses are useful for military applications, replacing damage-prone semiconductor or oxide windows. Sheets of the infrared-transparent polymer as disclosed may function as IR-transparent anti-fouling appliques for LWIR LiDARs. IR-transparent plastic panels can be disposed in front of sensors to protect them when being mounted on the outside of vehicles. IR-transparent composite panels may include an IR-transparent fiber in the composite, allowing easy inspection for damage.

FIG. 1 depicts an exemplary optical device 100, without limitation. In FIG. 1, incoming IR radiation 110 (which may or may not be present) strikes a lens 120. The lens 120 includes an IR-transparent polymer 130, optional filler particles 140, and an optional coating 150 that is disposed on the side exposed to the incident IR radiation 110. Transmitted IR radiation 160 will be present when there is incoming IR radiation 110. The transmitted IR radiation 160 may be focused onto, or otherwise directed to, an optional sensor 170. The sensor 170 may be linked to a processor or computer configured for processing data related to the sensed transmitted IR radiation 160 and/or other parameters of the optical device 100 during operation. The entire optical device 100 may be configured with an optional device housing 180, as shown in FIG. 1. The optical device 100 may be part of a larger optical system.

Some variations provide an optic containing at least 50 wt % of an infrared-transparent polymer, wherein the infrared-transparent polymer preferably has a carbon-free polymer backbone, wherein the optic is characterized by at least 80% average transmission of radiation over a wavenumber band with cumulative wavenumber width of at least 1000 $cm^{-1}$ contained within wavelengths from 3.1 µm to 5 µm and/or from 8.1 µm to 12 µm, and wherein the average transmission is defined as the ratio (expressed as a percentage) of radiation intensity through an optic thickness of 25 microns divided by incident radiation intensity. Note that the average transmission is an average over a range of wavelengths and may be calculated, for example, as the average value of the transmission in 0.1 micron increments of wavelength, or another increment of wavelength within the selected range of wavelengths.

The "cumulative wavenumber width" of a band is the total width, measured in wavenumbers, of one or more wavelengths from 3.1 µm to 5 µm or from 8.1 µm to 12 µm. For example, the wavenumber width of a band starting at 1200 $cm^{-1}$ and ending at 1000 $cm^{-1}$ is 1200−1000=200 $cm^{-1}$. Note that the cumulative wavenumber width can include multiple, distinct bands within wavelengths from 3.1 µm to 5 µm and/or from 8.1 µm to 12 µm. For example, the optic could be characterized by at least 80% average transmission of radiation over (i) a first wavenumber sub-band that is about 500 $cm^{-1}$ in width over wavelengths from 3.1 µm to 5 µm, and a (ii) a second wavenumber sub-band that is about 500 $cm^{-1}$ in width over wavelengths from 8.1 µm to 12 µm, totaling about 1000 $cm^{-1}$ in wavenumber width. Or, both a first and second wavenumber sub-band could be contained within wavelengths from 3.1 µm to 5 µm but be separated by a third wavenumber sub-band for which the optic has less than 80% average transmission of radiation.

In some embodiments, the optic is characterized by at least 80% average transmission of radiation over a wavenumber band with cumulative wavenumber width of at least 1500 $cm^{-1}$, or at least 2000 $cm^{-1}$, contained within wavelengths from 3.1 µm to 5 µm and/or from 8.1 µm to 12 µm.

The infrared-transparent polymer may be organic or inorganic. An organic infrared-transparent polymer may have a carbon-free polymer backbone but contain carbon in pendant groups. An inorganic infrared-transparent polymer may be a polyphosphazene-based polymer.

In some embodiments, the infrared-transparent polymer has a carbon-free polymer backbone that contains a plurality of polymer repeat units of the form

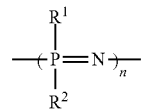

wherein $R^1$ is selected from the group consisting of halogens, alkyls, hydroxyl, amino, urea, thiol, thioether, amino alkyls, carboxylates, metals, metal-containing groups, and derivatives, deuterated forms, or combinations thereof;

wherein $R^2$ is selected from the group consisting of halogens, alkyls, hydroxyl, amino, urea, thiol, thioether, amino alkyls, carboxylates, metals, metal-containing groups, and derivatives, deuterated forms, or combinations thereof;

wherein n is selected from 2 to about 10,000; and wherein the carbon-free polymer backbone is linear, cyclic, branched, or a combination thereof.

In some embodiments, le and $R^2$ are independently selected from the group consisting of Cl, $CH_3$, $NH_2$, $NH(CH_2)_3CH_3$, $NH(CO)NH_2$, COOH, O(CO)OH, $OTi(OH)_3$, SH, and derivatives, deuterated forms, or combinations thereof.

In some embodiments, the carbon-free polymer backbone contains at least one polymer repeat unit of the form

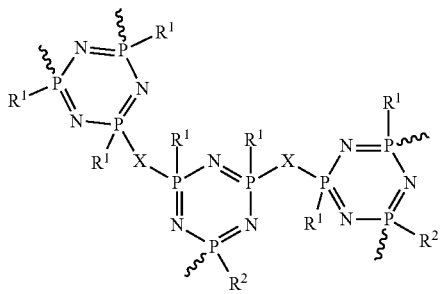

wherein $R^1$ is selected from the group consisting of halogens, alkyls, hydroxyl, amino, urea, thiol, thioether, amino alkyls, carboxylates, metals, metal-containing groups, and derivatives, deuterated forms, or combinations thereof;

wherein $R^2$ is selected from the group consisting of halogens, alkyls, hydroxyl, amino, urea, thiol, thioether, amino alkyls, carboxylates, metals, metal-containing groups, and derivatives, deuterated forms, or combinations thereof; and wherein X is a crosslinking group, and optionally wherein X is $R^1$ or $R^2$.

The carbon-free polymer backbone may be crosslinked with sulfur and/or with disulfide (S—S) bonds. The carbon-free polymer backbone may be crosslinked with dithiols. Alternatively, or additionally, the carbon-free polymer backbone may be crosslinked with $CH_2$, NH, NH(CO)NH, $COO-M^{2+}-OOC$, O(CO)O, $O-Ti(OH)_2-O$, or a combination thereof.

In some embodiments, the infrared-transparent polymer is a thermoset polymer. The infrared-transparent polymer may be characterized by a density from about 1.2 g/cm$^3$ to about 1.9 g/cm$^3$, for example. The infrared-transparent polymer may be characterized by an index of refraction from about 1.3 to about 1.9, for example.

In some variations, the optic includes, or is disposed in physical contact with, an anti-scratch layer, an anti-abrasion layer, an anti-reflection layer, or a combination thereof.

In some embodiments, the optic includes an anti-scratch layer that contains diamond, diamond-like carbon, sapphire, silicon, ZnS, or a combination thereof, for example. The anti-scratch layer may be disposed as a single layer or as multiple stacked layers.

In some embodiments, the optic includes an anti-reflection layer in the form of a stack of films that provides anti-reflection properties. The stack of films may be configured to provide anti-reflection properties over a band of interest, such as MWIR or LWIR. Typical anti-reflection layer materials are fluorides, which are usually IR-transparent, such as (but not limited to) $CaF_2$ or $PbF_2$.

In some embodiments, the optic includes an anti-rain erosion layer. The anti-rain erosion layer may contain an elastomeric material, such as (but not limited to) a polyphosphazene-based polymer, a polyphospazene-based copolymer, or a combination thereof. The elastomeric material may be covalently or physically bonded to the underlying optic. In some embodiments, the anti-rain erosion layer contains polyethylene and/or cyclic olefin polymers.

In certain embodiments, the elastomeric material has a storage modulus from about 1 MPa to about 500 MPa, such as from about 10 MPa to about 100 MPa, and a minimum elongation of 10%, 50%, 100%, 200%, or more.

The elastomeric material may be a thermoplastic comprising a polyphosphazene-based polymer or copolymer. Alternatively, the elastomeric material may be a thermoset comprising a polyphosphazene-based polymer or copolymer.

In some embodiments, the optic contains toughening filler particles, such as (but not limited to) toughening filler particles selected from the group consisting of Ge, $CaF_2$, NaCl, KCl, KBr, diamond, Si, CsI, MgO, $MgF_2$, LiF, NaF, $BaF_2$, ZnS, ZnSe, PbS, Pb Se, $PbF_2$, $LiYF_4$, $NaYF_4$, ThBrI, ThBrCl, and combinations thereof. The toughening filler particles may be in the form of spheres, rods, whiskers, platelets, or a combination thereof.

The toughening filler particles may have an average dimension selected from about 10 nm to about 500 μm. In certain embodiments, the toughening filler particles have an average dimension that is less than one-half of the thickness of the optic. The average dimension (e.g., diameter, effective diameter, or length) of the fillers may be chosen from ranges between 100 nm and 1 μm, between 1 μm and 10 μm, between 10 μm and 400 μm, or greater than 400 μm but less than one half of the thickness of the polymer component, in various embodiments.

The fillers may have a spherical geometry or they may have a geometric aspect ratio greater than 1 along one or more Cartesian axes (e.g. rods, whiskers, or platelets).

In certain embodiments, the toughening filler particles have an average volumetric loading from about 1 vol % to about 65 vol % based on volume of the polymer plus volume of the toughening filler particles. In various embodiments, the volumetric loading of the filler particulates within the polymer matrix may be chosen from ranges between 1-5% by volume, between 5-25% by volume, between 25-40% by volume, or between 40-65% by volume, for example.

The filler particles (when present) may be selected based upon their ability to toughen the underlying polymer matrix by means of crack tip blunting (reduced stress intensity factor), crack tip deflection (increased crack path length), or formation of local elastic heterogeneities that impose a residual compressive stress state around the fillers.

In some embodiments, the optic includes an anti-fouling layer on an exterior surface of the optic. An anti-fouling layer on the exterior surface resists the wetting and build-up of water, oils, dirt, and debris. The anti-fouling layer may contain a polyphosphazene-based polymer, a polyphospazene-based copolymer, or a combination thereof, for example. In some embodiments, the anti-fouling layer is a polyphosphazene polymer with one or more R groups that may be selected from $C_8$-$C_{22}$ hydrocarbons, fluorinated alkanes (e.g., 2,2,3,3,3-pentafluoropropylamine, 4,4,4-trifluorobutylamine, or 3,3,3-trifluoropropylamine). Synthesis of R groups may be through the amine version of the hydrocarbon (for example: P—Cl+$NH_2$-octyl P→NH-octyl). In some embodiments, the anti-fouling layer is polytetrafluoroethylene (PTFE) or fluorinated ethylene propylene (FEP), a copolymer of hexafluoropropylene and tetrafluoroethylene.

In various embodiments, the optic is a single lens, a compound lens, a window, an aperture, or an array of lenses. A lens may be converging, diverging, or collimating. A lens may create a point focus or a line focus (cylindrical lens). A lens may provide a circular image or be configured to provide rectangular coverage, to accommodate a rectangular format sensor, for example. A lens, window, or aperture may be flat, curved on one axis, biaxially curved, curved in three dimensions, or a combination thereof.

The dimensions of the optic may vary widely, including micrometer scale, millimeter scale, and meter scale. A typical diameter of an infrared-transparent lens, for example, is from about 1 mm to about 500 mm. A typical thickness of an infrared-transparent lens, for example, is from about 10 microns to about 100 mm. The optic may be disposed on an overall device or structure that may be very large, such as an airplane.

Preferred infrared-transparent polymers, for use in the optic, will now be described in further detail. Reference is made to the commonly owned patent application entitled "INFRARED-TRANSPARENT POLYMERS AND METHODS OF MAKING AND USING THE SAME" (Ser. No. 16/427,265) filed of even date herewith, and hereby incorporated by reference herein.

The present invention utilizes infrared-transparent (IR-transparent) polymers for at least part of an optic. As intended herein, an "infrared-transparent polymer" is a polymer that is infrared-transparent in at least one IR band. The infrared transparency is enabled by a carbon-free polymer backbone, as well as pendant groups and/or crosslinking molecules, that do not absorb medium wavelength infrared (MWIR) and/or long wavelength infrared (LWIR) light.

The infrared-transparent polymer may be crosslinked into a solid thermoset polymer. Common infrared-transparent polymers (such as polyethylene and polytetrafluoroethylene), in addition to having a carbon-containing backbone, are thermoplastic instead of thermoset (crosslinked). These conventional infrared-transparent polymers are thermoplastic because any changes, such as branching, in the backbone create infrared absorptions; thus, these conventional infrared-transparent polymers are not, in practice, subjected to crosslinking or thermosetting treatments. For example, high-density polyethylene is much less branched than low-density polyethylene and is more IR-transparent. By crosslinking a polymer, improved polymer hardness and therefore scratch resistance is obtained.

The infrared-transparent polymers disclosed herein, especially when crosslinked, provide better cracking resistance (higher work of fracture) compared to inorganic IR-transparent materials and improved scratch resistance (hardness) compared to current IR-transparent polymers. Durable and scratch-resistant materials are desired for MWIR and/or LWIR windows and optics, for example.

In this disclosure a "polymer" means a large molecule, or macromolecule, composed of at least two repeat subunits. The number of repeat subunits may be in principle any number greater than 2, but typically is limited to about 10,000. In various embodiments, the number of repeat subunits (also known as the degree of polymerization) is 2, 3, 4, 5, about 10, about 50, about 100, about 200, about 500, about 1,000, about 2,000, or about 5,000. The polymer may be linear, branched, cyclic, crosslinked, or a combination thereof. The polymer is typically a solid but can also be a liquid, depending on molecular weight, degree of crosslinking, and external conditions such as temperature. A "crosslink" is a bond that links one polymer chain to another. The crosslinking bonds may be covalent bonds, ionic bonds, or a combination thereof.

In this disclosure, the MWIR band refers to infrared light wavelengths from 3.1 μm to 5 μm, corresponding to infrared light wavenumbers (the number of waves per unit distance) from about 3200 cm$^{-1}$ to about 2000 cm$^{-1}$, respectively. In this disclosure, the LWIR band refers to infrared light wavelengths from 8.1 μm to 12 μm, corresponding to infrared light wavenumbers from about 1200 cm$^{-1}$ to about 800 cm$^{-1}$, respectively. LWIR waves have less energy and therefore lower frequency, giving longer wavelengths and smaller wavenumbers. The wavenumber times the speed of light is the wave frequency.

Some variations of this invention are based on polymer backbones known as polyphosphazenes, which have a repeating —(R'—P(—R$^2$)=N— structure:

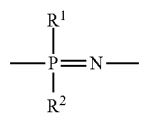

Polyphosphazenes are known polymers (see, for example, Allcock, "The Synthesis of Functional Polyphosphazenes and their Surfaces", *Appl. Organometal. Chem.* 12, 659-666, 1998), which is hereby incorporated by reference herein. Polyphosphazene polymers are commercially available as aerospace elastomers with R', R$^2$, or pendant groups attached to R$^1$ and/or R$^2$ that are infrared-absorbing (not infrared-transparent). While there are known UV-transparent polyphosphazenes and NIR-transparent polyphosphazenes, there are heretofore no known MWIR-transparent or LWIR-transparent modified polyphosphazene polymers.

Some variations herein are predicated on the realization that the polyphosphazene backbone itself is appropriate for IR transparency, and that R$^1$, R$^2$, or pendant groups attached to R$^1$ and/or R$^2$ may be modified, reduced, or removed in order to minimize or eliminate infrared absorption within the polymer. It has been discovered that certain modifications to polyphosphazene polymers make them MWIR-transparent and/or LWIR-transparent.

By "infrared-transparent" it is not necessarily meant completely infrared transparent; some absorption of thermal infrared radiation may occur. In particular, "transparent" means a sheet of polymer with known thickness (such as 25 microns) absorbs less than 50%, preferably about 40% or less, more preferably about 30% or less, and most preferably about 20% or less, of incident infrared light at a wavelength of interest. If a wavelength range is used, the transmission is averaged over that range. Incident light is normal (perpendicular) to the surface of the polymer sheet.

Regular transmission of infrared light at a selected wavelength can be determined for a sample 25 microns (about 0.001 inch) thick, or for another thickness of interest, as I(t)$_0$, where I$_0$ is the incident intensity and I(t) is the intensity as a function of thickness. I(t)/I$_0$ at a given panel thickness can be experimentally determined, for example, using a Perkin Elmer IR spectrometer. It is noted that one of ordinary skill in the art will understand that transmission generally can include regular transmission and diffuse transmission, both of which can contribute to total transmission. The average transmission values in this specification include only regular transmission.

Some variations utilize an infrared-transparent polymer having a carbon-free polymer backbone, wherein the infrared-transparent polymer is characterized by a density from about 1.2 g/cm$^3$ to about 1.9 g/cm$^3$, an index of refraction from about 1.3 to about 1.9, and at least 70%, at least 80%, or at least 90%, average transmission of radiation at wavelengths from 3.1 μm to 5 μm and/or from 8.1 μm to 12 μm, wherein the average transmission is defined as the ratio (expressed as a percentage) of radiation intensity through an infrared-transparent polymer thickness of 25 microns divided by incident radiation intensity.

In some embodiments, the infrared-transparent polymer is characterized by at least 70% average transmission of radiation at wavelengths from 3.1 μm to 5 μm. In certain embodiments, the infrared-transparent polymer is characterized by at least 70% average transmission of radiation at wavelengths specifically from 4 μm to 5 μm.

In some embodiments, the infrared-transparent polymer is characterized by at least 70% average transmission of radiation at wavelengths from 8.1 μm to 12 μm. In certain embodiments, the infrared-transparent polymer is characterized by at least 70% average transmission of radiation at wavelengths specifically from 8.1 μm to 10 μm.

The infrared-transparent polymer may be characterized by the absence of an IR absorption peak having (i) a height of at least 5% absorption and (ii) a full-width at half maximum less than 300 cm$^{-1}$, at any wavelengths from 3.1 μm to 5 μm and/or from 8.1 μm to 12 μm.

The "full-width at half maximum" is an expression of the extent given by the difference between the two extreme values of the independent variable (wavenumber) at which the dependent variable (absorption) is equal to half of its maximum value. In other words, it is the width of a spectrum curve measured between those points on the y-axis which are half the maximum amplitude. The full-width is on the wavenumber axis and the half maximum is on the absorption axis.

Therefore, for an IR absorption peak to count against the polymer being infrared-transparent, that peak must have a significant height (at least 5% absorption intensity compared to a reference with total transmission and no absorption) as well as be a narrow peak, rather than a broad, plateau-like signal. The preferred cut-off for a narrow peak is a full-width at half maximum peak size less than 300 cm$^{-1}$. Peaks that have a full-width at half maximum greater than 300 cm$^{-1}$ are regarded as broad, baseline signals that do not indicate IR absorption for purposes of this disclosure. These broad, baseline signals can arise from phenomena other than bond vibrations within the polymer, from the presence of impurities, or for other reasons.

The infrared-transparent polymer may also (or instead) be characterized by an average absorption coefficient of less than 75 cm$^{-1}$ for wavelengths from 3.1 μm to 5 μm and/or from 8.1 μm to 12 μm. Transmission characteristics in the infrared range can be quantified as absorption coefficient values. The absorption coefficient can be determined using the following relationship: $\alpha = 4\pi k/\lambda$, where $\alpha$ is the absorption coefficient, $\lambda$ is the wavelength, and k is the imaginary portion of the complex index of refraction (n+ik), where n is the ordinary refractive index and i is the square root of −1. The complex refractive index of a material may be determined using the mathematical Kramers-Kronig relationship. Since n and k are known for a given material, α can be calculated for a selected wavelength. For a range of wavelengths, the average value of α can be calculated, e.g. $\alpha=75$ cm$^{-1}$ for wavelengths from 3.1 μm to 5 μm.

In some embodiments, the infrared-transparent polymer contains P, N, H, and optionally S, and does not contain C. In other embodiments, the infrared-transparent polymer contains P, N, C, O, and optionally S, and does not contain H. In other embodiments, the infrared-transparent polymer contains P, N, C, O, H, and optionally S.

In some embodiments, the infrared-transparent polymer contains P, N, O, H, and an additional inorganic species. The additional inorganic species may be selected from the group consisting of Si, Al, Hf, Zr, Ti, and combinations thereof, for example. The additional inorganic species may be covalently bonded to the P through an oxygen atom.

In some embodiments, the infrared-transparent polymer further contains a cation with a charge of +1 or higher. The cation may be an alkali metal (e.g., Na$^+$), an alkaline earth metal (e.g., Ca$^{2+}$), or a transition metal (e.g., Ti$^{n+}$, n=1 to 4), for example.

In some preferred embodiments of infrared-transparent polymers, a carbon-free polymer backbone contains a plurality of polymer repeat units of the form

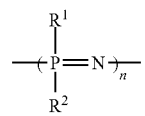

wherein R$^1$ is selected from the group consisting of halogens, alkyls, hydroxyl, amino, urea, thiol, thioether, amino alkyls, carboxylates, metals, metal-containing groups, and derivatives, deuterated forms, or combinations thereof;

wherein R$^2$ is (independently from R') selected from the group consisting of halogens, alkyls, hydroxyl, amino, urea, thiol, thioether, amino alkyls, carboxylates, metals, metal-containing groups, and derivatives, deuterated forms, or combinations thereof;

wherein n is selected from 2 to about 10,000; and wherein the carbon-free polymer backbone is linear, cyclic, branched, or a combination thereof.

In this disclosure, superscripts denote R group identity and subscripts denote R group quantity. When R$^1$=R$^2$=R, the repeat unit is —R$_2$P=N—, wherein each of the two (identical) R groups is bonded directly to P and not to N, which itself is double-bonded to P. Also note that in some polymers, different R groups are present on different repeat units, so that a given polymer may contain more than two unique pendant groups.

In some embodiments, le is selected from the group consisting of Cl, CH$_3$, NH$_2$, NH(CH$_2$)$_3$CH$_3$, NH(CO)NH$_2$, COOH, COOD, O(CO)OH, OTi(OH)$_3$, SH, and derivatives, deuterated forms, or combinations thereof. In these or other embodiments, R$^2$ is selected from the group consisting of Cl, CH$_3$, NH$_2$, NH(CH$_2$)$_3$CH$_3$, NH(CO)NH$_2$, COOH, COOD, O(CO)OH, OTi(OH)$_3$, SH, and derivatives, deuterated forms, or combinations thereof.

In certain embodiments, le and/or R$^2$ is a C$_1$-C$_{22}$ hydrocarbon, for example. The C$_1$-C$_{22}$ hydrocarbon may be an alkyl, olefin, or aromatic group (or a combination thereof), may be linear, branched, or cyclic (or a combination thereof), and may be substituted (i.e. one or more hydrogen atoms replaced with other atoms, such as a halogen). Synthesis may proceed through the amine version of the hydrocarbon, such as (for the case of a C$_8$ alkyl group): P—Cl+ NH$_2$-octyl P—NH-octyl. In certain embodiments, le and/or R$^2$ is fluorinated alkane, such as 2,2,3,3,3-pentafluoropropylamine, 4,4,4-trifluorobutylamine, or 3,3,3-trifluoropropylamine.

Depending on the choice of R$^1$ and R$^2$, and to some extent the degree of polymerization, the infrared-transparent polymer may have a range of densities. In various embodiments, the infrared-transparent polymer has a density from about 1 g/cm$^3$ to about 2 g/cm$^3$, such as about 1.2, 1.3, 1.4, 1.5, 1.6, 1.7, 1.8, or 1.9 g/cm$^3$, measured at 25° C.

Depending on the choice of $R^1$ and $R^2$, and to some extent the degree of polymerization, the infrared-transparent polymer may have a range of index of refraction. In various embodiments, the infrared-transparent polymer has a normal index of refraction from about 1 to about 2, such as about 1.3, 1.4, 1.5, 1.6, 1.7, 1.8, or 1.9, measured at 25° C. Note that the tunability of index of refraction of the infrared-transparent polymer, by altering the selection of $R^1$ and $R^2$, is a beneficial property for many applications.

The carbon-free polymer backbone may be crosslinked, if desired, to form a thermoset polymer. Note that the $R^1$ groups and/or the $R^2$ groups can act as crosslinking groups within the overall polymer. See, for instance, FIGS. 1 to 4 for examples of crosslinking reactions involving possible $R^1/R^2$ pendant groups. Amine ($NH_2$), urea, carboxylic acid (COOH), COO-$M^+$ ($M^+$ is a +1 oxidation-state cation, such as $Na^+$), O(CO)OH, $Ti(OH)_3$, and —SH groups, for example, may be used for crosslinking to connect two or more polyphosphazene chains.

In some embodiments, the carbon-free polymer backbone is crosslinked with sulfur and/or with disulfide (S—S) bonds. The carbon-free polymer backbone may be crosslinked with dithiols. In these or other embodiments, the carbon-free polymer backbone is crosslinked with $CH_2$, NH, NH(CO)NH, COO-$M^{2+}$-OOC, O(CO)O, O—$Ti(OH)_2$—O, or a combination thereof.

In some crosslinked infrared-transparent polymers, the carbon-free polymer backbone contains at least one polymer repeat unit of the form

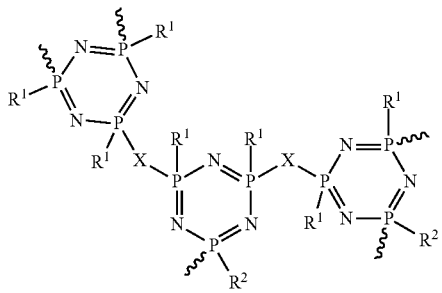

wherein $R^1$ is selected from the group consisting of halogens, alkyls, hydroxyl, amino, urea, thiol, thioether, amino alkyls, carboxylates, metals, metal-containing groups, and derivatives, deuterated forms, or combinations thereof;

wherein $R^2$ is selected from the group consisting of halogens, alkyls, hydroxyl, amino, urea, thiol, thioether, amino alkyls, carboxylates, metals, metal-containing groups, and derivatives, deuterated forms, or combinations thereof; and wherein X is a crosslinking group, and optionally wherein X is $R^1$ or $R^2$.

In some embodiments, the infrared-transparent polymer is characterized by a work of fracture of at least 75 $J/m^2$ and/or a Knoop hardness of at least 50 MPa. The "work of fracture" characterizes the toughness of the polymer and is the energy required to propagate a crack in the polymer. The work of fracture may be measured using an Instron tensile-testing machine, for example. See Smith III et al., "Estimation of fracture energy from the work of fracture and fracture surface area: I. Stable crack growth" *Int J Fract* (2009) 156:97-102, which is hereby incorporated by reference herein for its teachings of measuring the work of fracture.

Knoop hardness is a well-known measurement. Knoop hardness is calculated by measuring the indentation produced by a diamond tip that is pressed onto the surface of a sample. See Knoop et al., "A Sensitive Pyramidal-Diamond Tool for Indentation Measurements" *Journal of Research of the National Bureau of Standards* (1939) 23 (1): 39-61 (Research Paper RP1220), which is hereby incorporated by reference herein for its teachings of measuring the Knoop hardness.

Figure 6:
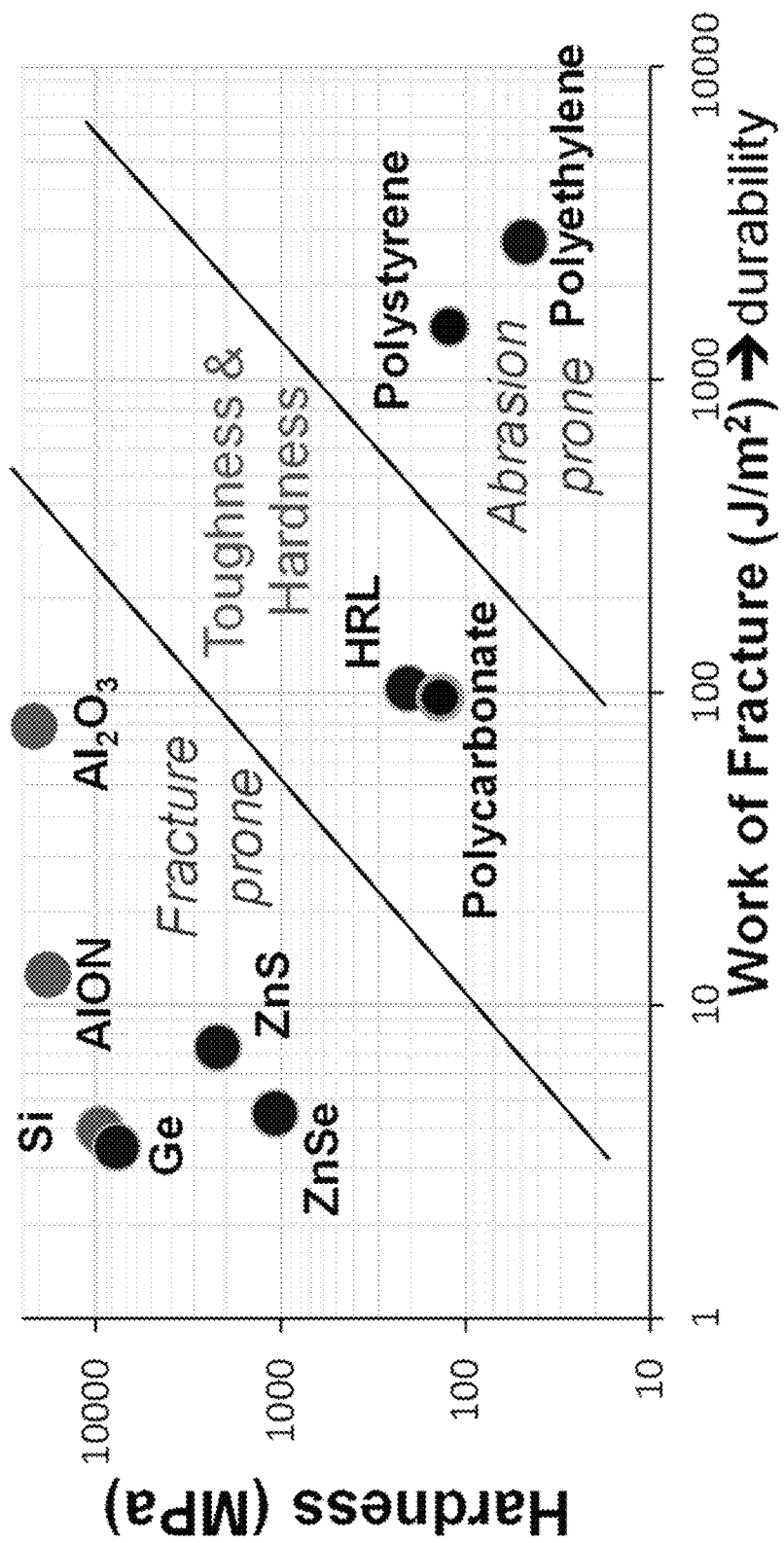
FIG. 6 is a plot of hardness versus work of fracture for prior-art materials compared to an exemplary material (labeled "HRL") provided in some embodiments of the present invention.

In various embodiments, the infrared-transparent polymer is characterized by a work of fracture of at least 10, 25, 50, 75, or 100 $J/m^2$. In these or other embodiments, the infrared-transparent polymer is characterized by a Knoop hardness of at least 10, 25, 50, 100, 200, 300, or 400 MPa. In a particular embodiment depicted in FIG. 6, an infrared-transparent polymer (labeled "HRL") is characterized by a work of fracture of about 100 $J/m^2$ and/or a Knoop hardness of about 200 MPa. In some embodiments, the infrared-transparent polymer is characterized by a Knoop hardness less than 500 MPa or less than 1000 MPa.

In some embodiments, the infrared-transparent polymer further includes one or more filler particles physically blended with the polymer. The concentration of filler particles may vary, such as from about 0.1 wt % to about 50 wt % on the basis of the overall composition (infrared-transparent polymer+filler particles).

Filler particles for use in the compositions of the present disclosure preferably exhibit high IR transparency and small particle size relative to incident radiation wavelength in order to increase IR transparency and limit scattering. In particular, the filler particles material may be chosen so as to be transparent in the MWIR and/or LWIR bands. However, the present invention is not limited to filler particles (when present) that are transparent in the MWIR and/or LWIR bands. If the concentration of filler particles is relatively low (e.g., less than about 30 wt %, 20 wt %, 10 wt %, 5 wt %, or 1 wt %), the filler particles may lack transparency in the MWIR and/or LWIR bands, while the overall material (polymer+filler particles) has at least 70% average transmission of radiation at wavelengths from 3.1 μm to 5 μm and/or from 8.1 μm to 12 μm.

Suitable filler particles include, but are not limited to, Ge (germanium), $CaF_2$, NaCl, KCl, KBr, diamond, Si, CsI, MgO, $MgF_2$, LiF, NaF, $BaF_2$, ZnS, ZnSe, PbS, Pb Se, $PbF_2$, $LiYF_4$, $NaYF_4$, thallium bromoiodide (ThBrI), and thallium bromochloride (ThBrCl), and combinations thereof.

Filler particles for use in the compositions of the present disclosure may be selected in the nanoparticle size range. In some embodiments, the filler particles have an average discrete particle size ranging from about 10 nm to about 1000 nm, such as from about 100 nm to about 500 nm. Particles sizes may be measured by a variety of techniques, including dynamic light scattering, laser diffraction, image analysis, or sieve separation, for example. Dynamic light scattering is a non-invasive, well-established technique for measuring the size and size distribution of particles typically in the submicron region, and with the latest technology down to 1 nanometer. Laser diffraction is a widely used particle-sizing technique for materials ranging from hundreds of nanometers up to several millimeters in size. Exemplary dynamic light scattering instruments and laser diffraction instruments for measuring particle sizes are available from Malvern Instruments Ltd., Worcestershire, UK. Image analysis to estimate particle sizes and distributions can be done directly on photomicrographs, scanning electron micrographs, or other images.

Other variations of the invention utilize, for the optic, an infrared-transparent polymer containing a plurality of polymer repeat units of the form

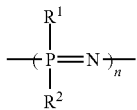

wherein $R^1$ is selected from the group consisting of halogens, alkyls, hydroxyl, amino, urea, thiol, thioether, amino alkyls, carboxylates, metals, metal-containing groups, and derivatives, deuterated forms, or combinations thereof;

wherein $R^2$ is selected from the group consisting of halogens, alkyls, hydroxyl, amino, urea, thiol, thioether, amino alkyls, carboxylates, metals, metal-containing groups, and derivatives, deuterated forms, or combinations thereof;

wherein n is selected from 2 to about 10,000; and wherein the plurality of polymer repeat units is linear, cyclic, branched, or a combination thereof.

In some embodiments, the infrared-transparent polymer is characterized by at least 70% average transmission of radiation at wavelengths from 3.1 μm to 5 μm and/or from 8.1 μm to 12 μm, wherein the average transmission is defined as the ratio (expressed as a percentage) of radiation intensity through an infrared-transparent polymer thickness of 25 microns divided by incident radiation intensity.

In certain embodiments, the infrared-transparent polymer is characterized by at least 70%, at least 80%, or at least 90% average transmission of radiation at wavelengths specifically from 3 μm to 4 μm.

In certain embodiments, the infrared-transparent polymer is further characterized by at least 70%, at least 80%, or at least 90% average transmission of radiation at wavelengths from 0.2 μm to 2 μm.

In some infrared-transparent polymers, le and $R^2$ are each independently selected from the group consisting of Cl, $CH_3$, $NH_2$, $NH(CH_2)_3CH_3$, $NH(CO)NH_2$, COOH, COOD, $O(CO)OH$, $OTi(OH)_3$, SH, and derivatives, deuterated forms, or combinations thereof.

At least a portion of the infrared-transparent polymer may be crosslinked, such as with sulfur and/or with disulfide (S—S) bonds. Alternatively, or additionally, at least a portion of the infrared-transparent polymer may be crosslinked with dithiols, $CH_2$, NH, NH(CO)NH, $COO\text{-}M^{2+}\text{-}OOC$, $O(CO)O$, $O\text{—}Ti(OH)_2\text{—}O$, or a combination thereof.

In some embodiments, the infrared-transparent polymer contains at least one polymer repeat unit of the form

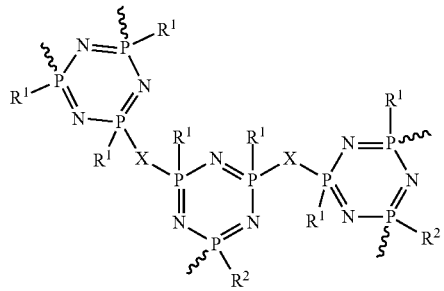

wherein X is a crosslinking group, and optionally wherein X is $R^1$ or $R^2$.

The repeat unit

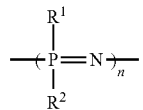

is free of carbon atoms in the backbone, but carbon may be contained in one or more R pendant groups. It should be noted that other repeat units may be contained in the polymer (e.g., as a copolymer or as a polymer blend), where the other repeat units may contain carbon in the backbone. In some preferred embodiments, the infrared-transparent polymer does not include a cyclic olefin copolymer. Preferably, the entire polymer has a carbon-free backbone, but that is not strictly necessary, depending on the level of IR transparency that is desired.

In some preferred embodiments, the infrared-transparent polymer does not contain chiral polyphosphazenes. Chirality can cause IR absorption and thus reduce the IR transparency.

Synthesis Methods

Exemplary synthesis methods to produce the disclosed infrared-transparent polymers include, but are not limited to, the following methods.

In some methods, ring-opening polymerization (ROP) of hexachlorocyclophosphazene (HCCP) is utilized. Ring-opening polymerization may be performed neat (in the melt) or in solution following literature procedures to yield poly (dichlorophosphazene) (PDCP) which may then be modified with the desired side groups. See, for example, Mujumdar et al., "A study of solution polymerization of polyphosphazenes" *Macromolecules,* 1990, 23, 14, which is incorporated by reference. Also see Allcock, "The Synthesis of Functional Polyphosphazenes and their Surfaces" *Appl. Organometal. Chem.,* 12, 659-666, 1998, which is incorporated by reference. There are many literature procedures for substituting the Cl groups on the polyphosphazene backbone. See Andrianov et al., "Poly(dichlorophosphazene) As a Precursor for Biologically Active Polyphosphazenes: Synthesis, Characterization, and Stabilization" *Macromolecules* 2004, 37, 414-420, which is incorporated by reference, for its teachings of introducing hydroxyl groups via the addition of water to PDCP. See Allcock, "The Synthesis of Functional Polyphosphazenes and their Surfaces" *Applied Organometallic Chemistry* 1998, 12 (10-11), 659-666, which is incorporated by reference, for its Scheme 1B for adding carbonate groups via the addition of sodium carbonate to PDCP. See Rothemund et al., "Preparation of polyphosphazenes" *Chemical Society Reviews* 2016, 45 (19), 5200-5215, for its FIG. 9 showing a technique to introduce methyl groups from the cationic polymerization of $Cl\text{—}P(CH_3)_2\text{=}N\text{—}Si(CH_3)_3$.

Figure 2:
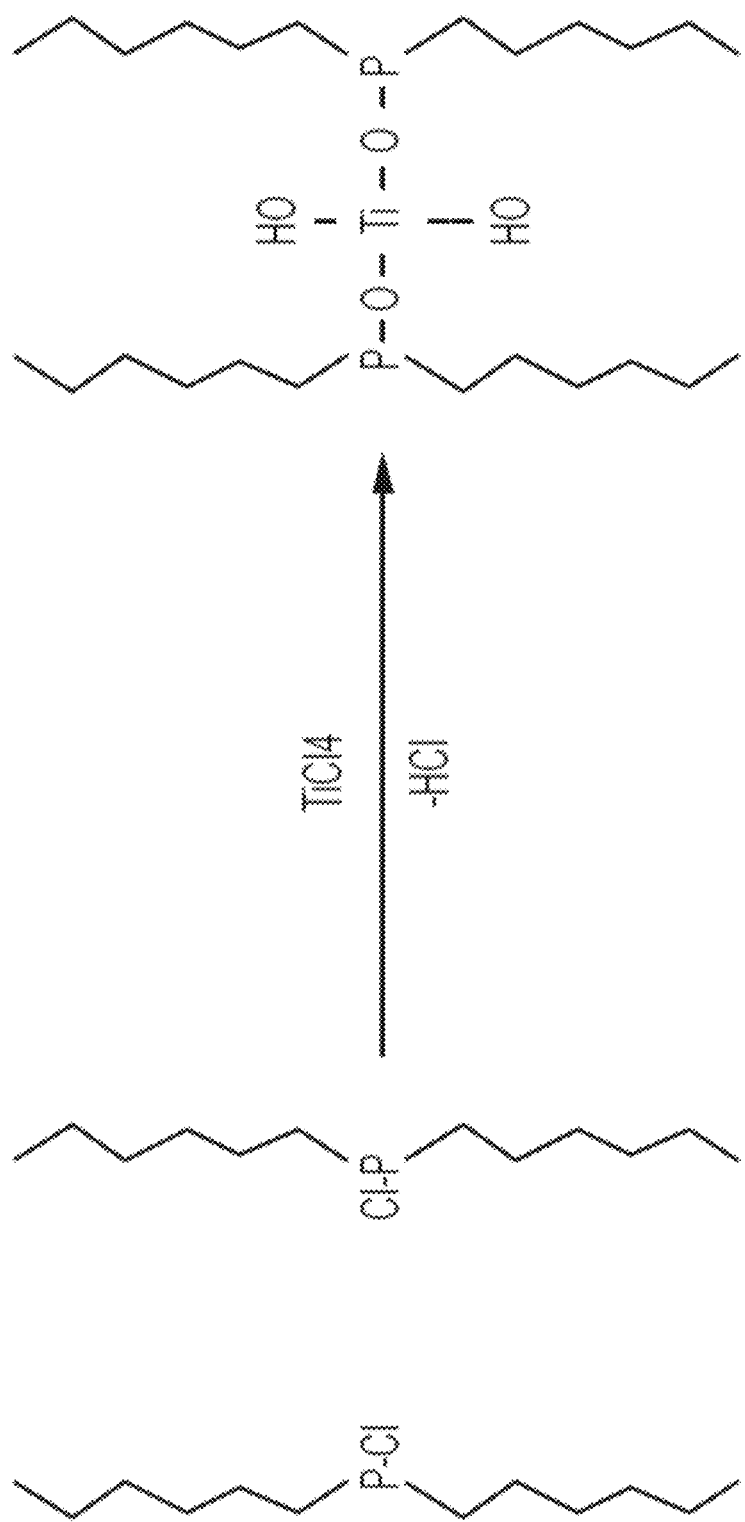
FIG. 2 is a reaction sketch for a method of titanium (Ti) crosslinking of poly(dichlorophosphazene), in some embodiments.

Some embodiments relate to titanium (Ti) crosslinking of PDCP, as depicted in FIG. 2. In an exemplary method, without limitation, titanium isopropoxide and poly(dichlorophosphazene) are suspended in dry ethanol. Titanium(IV) isopropoxide is added in a 1:1 molar ratio with Cl, to the solution. Acid is optionally added in a ratio of 0.01 to 0.3 mol acid per mol titanium(IV) isopropoxide. Then water is added to cause condensation of the alkoxide in a 1:1 to 1:20 alkoxide:water ratio. The alkoxide:water ratio is preferably from about 1:2 to about 1:10, such as about 1:3 ratio. Successful linking of Si alkoxides to polyphosphazenes has been shown in Guglielmi et al., "Hybrid materials based on metal oxides and poly(organophosphazenes)" *J Inorg Organomet Polym* (1996) 6: 221, which is incorporated by reference; this reaction only occurs if the PDCP is modified to have hydroxides on pendant groups and then the silicon alkoxide is mixed with the modified PDCP prior to the addition of water. Without being limited by speculation, the present inventors do not believe the PDCP first needs hydroxide groups if the more reactive chloride groups are present. However, if hydroxides are desired, the PDCP can be first reacted with water in a 1:1 water:Cl molar ratio to create hydroxides prior to mixing with an alkoxide. Lastly, this method applies to all metal alkoxides such as aluminum isopropoxide, aluminum ethoxide, aluminum butoxide, tetraethylorthosilicate, zirconium isopropoxide, and so on—not just titanium alkoxide. FIG. 2 shows the specific case of the metal being Ti.

Figure 3:
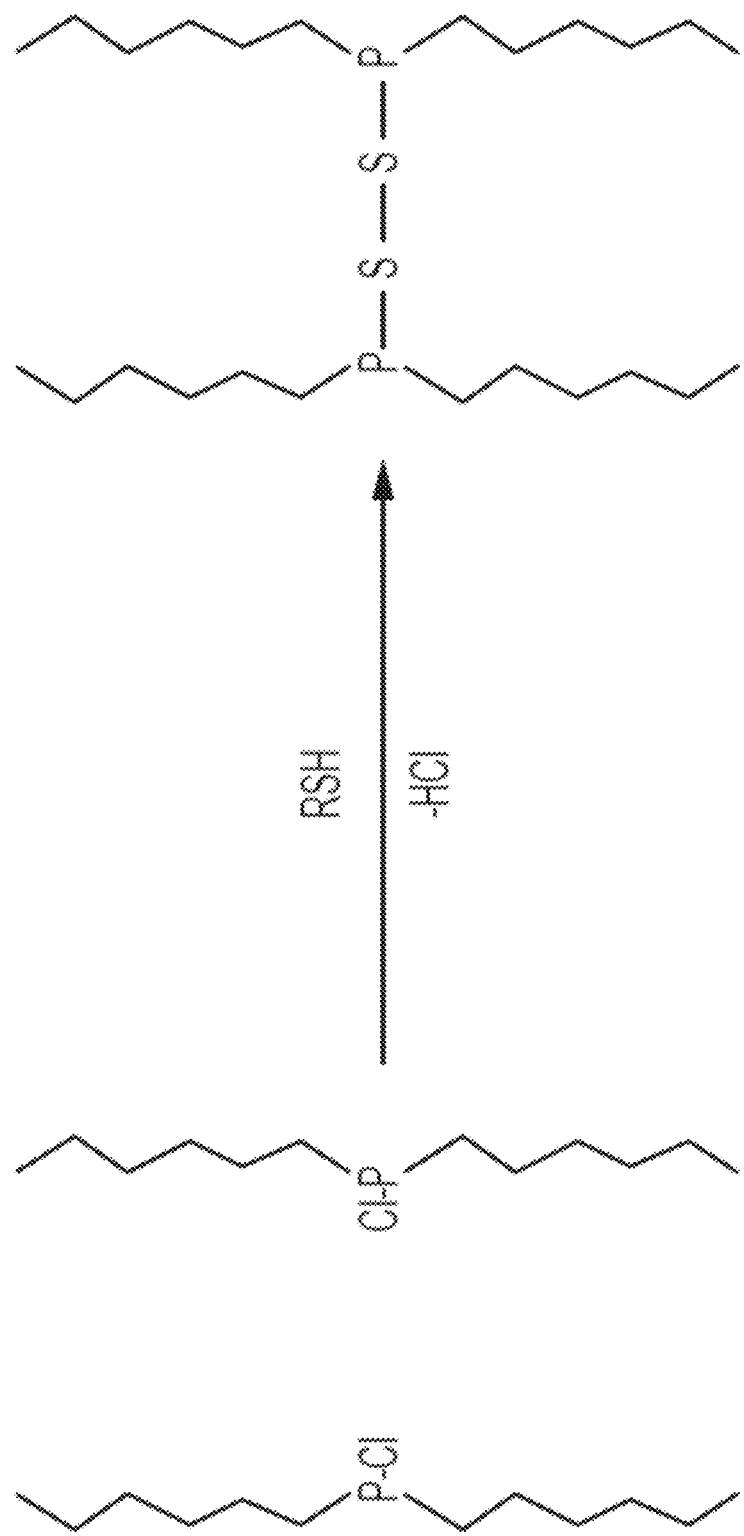
FIG. 3 is a reaction sketch for a method of S—S (disulfide) crosslinking of poly(dichlorophosphazene), in some embodiments.
Figure 4:
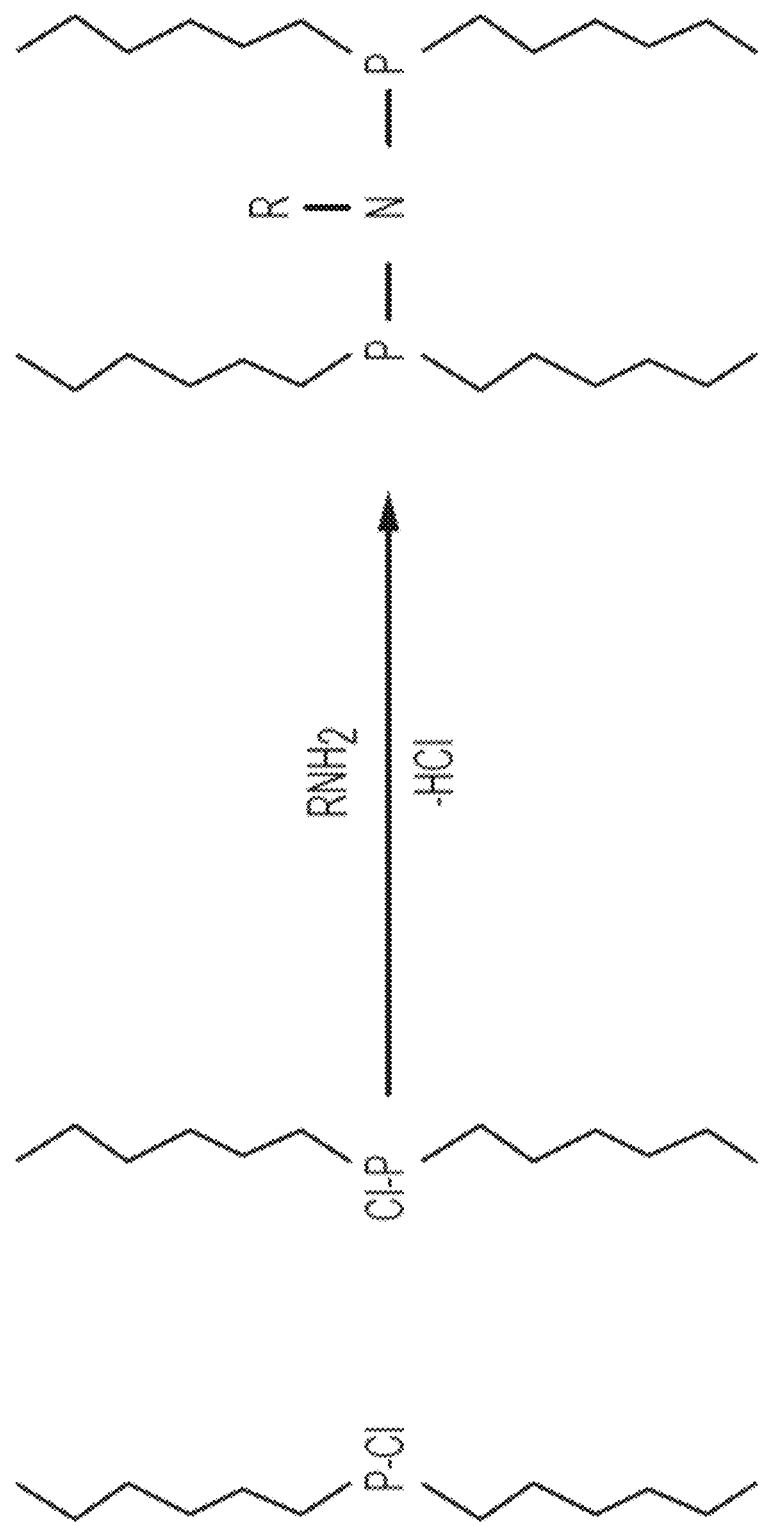
FIG. 4 is a reaction sketch for a method of using ammonia ($NH_3$) or other $NH_2$-containing group to achieve crosslinking of poly(dichlorophosphazene), in some embodiments.

Some embodiments relate to S—S (disulfide) crosslinking of PDCP, as depicted in FIG. 3. In an exemplary method, without limitation, poly(dichlorophosphazene) is diluted in dry tetrahydrofuran. Thioacetic acid is added dropwise to the solution in a 1:1.2 molar ratio of chloride groups to thioacetic acid. Base is optionally added to help accelerate the reaction. The mixture is allowed to stir at room temperature (or at reflux) for 2 to 16 hr or until thioacetic acid is fully reacted with poly(dichlorophosphazene). The THF may be removed before the addition of ethyl acetate. The polymer is washed with basic solution (3×) and water (3×) to remove excess thioacetic acid. The ethyl acetate solution is then dried with a sulfate salt (such as $MgSO_4$ or $Na_2SO_4$) and filtered. The organic solvent is then removed by rotary evaporation or high vacuum to yield a poly(diethanethioatephospazene). The acetate groups are removed by refluxing polymer in alcohol with sodium hydroxide. The mixture is acidified back to neutral pH. The polymer is extracted with ethyl acetate or other organic solvent. The organic layer is washed with water (3×). Residue water is removed with sulfate salt. The organic solvent is then removed by rotary evaporation or high vacuum to yield a poly(dimercaptophospazene). The polymer is then crosslinked by oxidation of thiol groups to disulfide linkages.

Some embodiments relate to dithiol crosslinking of PDCP. In an exemplary method, without limitation, the polymer may be crosslinked using alkyldithiols (e.g., ethanedithiol, propanedithiol, butanedithiol, thiodiethanethiol, etc.) and adding them directly to poly(dichlorophosphazene) or in a diluted solution in dry solvent (such as tetrahydrofuran or ethyl acetate). The alkyldithiol will be added in a 1:1 molar ratio of thiols to chlorides. Base is optionally added to help drive the reaction forward.

See Allcock, "CROSS-LINKING REACTIONS FOR THE CONVERSION OF POLYPHOSPHAZENES INTO USEFUL MATERIALS" OFFICE OF NAVAL RESEARCH Technical Report No. 23, May 18, 1994, which is incorporated by reference, for its techniques to crosslink polyphosphazenes and specifically for adding amines via addition of ammonia to PDCP. See, for example, FIG. 4 with R=H for the specific case of using ammonia ($NH_3$) to achieve crosslinking.

Figure 5:
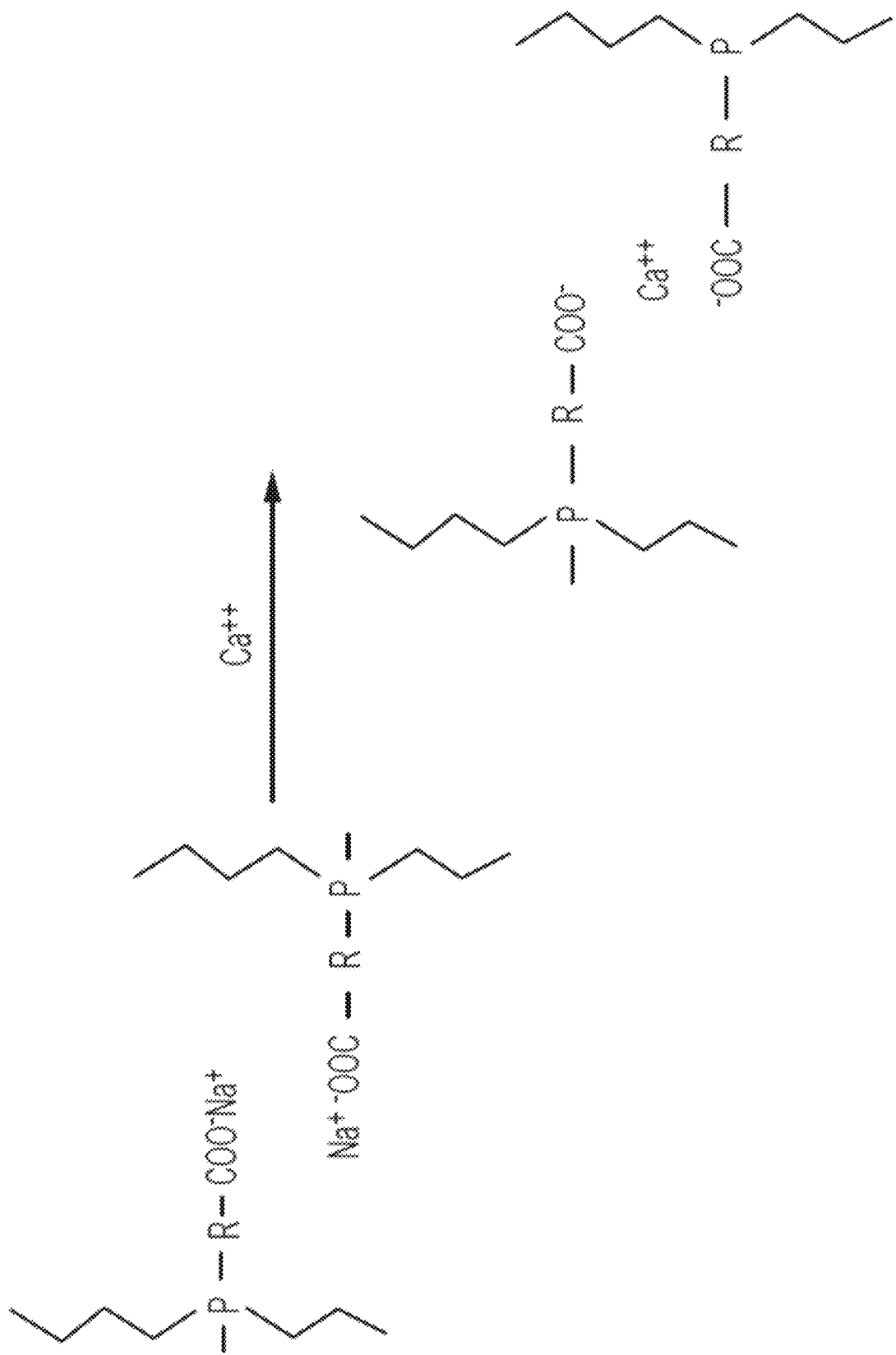
FIG. 5 is a reaction sketch for a method of carboxylate crosslinking of poly(dichlorophosphazene), in some embodiments.

Some embodiments relate to carboxylate crosslinking of PDCP, as depicted in FIG. 5. In this method, a polymer containing sodium carboxylate groups ($COO^-Na^+$) is reacted with calcium ions ($Ca^{2+}$), each of which replaces two sodium ions that have a charge of +1. This scheme produces ionic crosslinks anchored by the calcium divalent cation, as shown in FIG. 5. Note that R may be O, S, or alkyl (e.g., methyl or ethyl), for example. R may be absent, in which case the sodium carboxylate group is bonded directly to the P atom. Also, other monovalent and divalent metal ions may be employed, in place of (or in addition to) sodium and calcium, respectively.

In this detailed description, reference has been made to multiple embodiments and to the accompanying drawings in which are shown by way of illustration specific exemplary embodiments of the invention. These embodiments are described in sufficient detail to enable those skilled in the art to practice the invention, and it is to be understood that modifications to the various disclosed embodiments may be made by a skilled artisan.

Where methods and steps described above indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

All publications, patents, and patent applications cited in this specification are herein incorporated by reference in their entirety as if each publication, patent, or patent application were specifically and individually put forth herein.

The embodiments, variations, and figures described above should provide an indication of the utility and versatility of the present invention. Other embodiments that do not provide all of the features and advantages set forth herein may also be utilized, without departing from the spirit and scope of the present invention. Such modifications and variations are considered to be within the scope of the invention defined by the claims.

What is claimed is:

1. An optic containing at least 50 wt % of an infrared-transparent polymer, wherein said infrared-transparent polymer has a carbon-free polymer backbone, wherein said optic is characterized by at least 80% average transmission of radiation over a wavenumber band with cumulative wavenumber width of at least 1000 $cm^{-1}$ contained within wavelengths from 3.1 μm to 5 μm and/or from 8.1 μm to 12 μm, and wherein said average transmission is defined as the ratio (expressed as a percentage) of radiation intensity through an optic thickness of 25 microns divided by incident radiation intensity.

2. The optic of claim 1, wherein said optic is a single lens, a compound lens, a window, or an array of lenses.

3. The optic of claim 2, wherein said optic is a lens or window that is flat, is curved on one axis, is biaxially curved, is curved in three dimensions, or is a combination thereof.

4. The optic of claim 1, wherein said cumulative wavenumber width is at least 1500 $cm^{-1}$ contained within wavelengths from 3.1 μm to 5 μm and/or from 8.1 μm to 12 μm.

5. The optic of claim 1, wherein said cumulative wavenumber width is at least 2000 $cm^{-1}$ contained within wavelengths from 3.1 μm to 5 μm and/or from 8.1 μm to 12 μm.

6. The optic of claim 1, wherein said carbon-free polymer backbone contains a plurality of polymer repeat units of the form

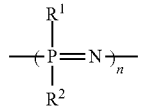

wherein R¹ is selected from the group consisting of halogens, alkyls, hydroxyl, amino, urea, thiol, thio-ether, amino alkyls, carboxylates, metals, metal-containing groups, and derivatives, deuterated forms, or combinations thereof;

wherein R² is selected from the group consisting of halogens, alkyls, hydroxyl, amino, urea, thiol, thio-ether, amino alkyls, carboxylates, metals, metal-containing groups, and derivatives, deuterated forms, or combinations thereof;

wherein n is selected from 2 to about 10,000; and wherein said carbon-free polymer backbone is linear, cyclic, branched, or a combination thereof.

7. The optic of claim 6, wherein R¹ and R² are independently selected from the group consisting of Cl, $CH_3$, $NH_2$, $NH(CH_2)_3CH_3$, $NH(CO)NH_2$, COOH, O(CO)OH, $OTi(OH)_3$, SH, and derivatives, deuterated forms, or combinations thereof.

8. The optic of claim 1, wherein said carbon-free polymer backbone contains at least one polymer repeat unit of the form

[chemical structure]

wherein R¹ is selected from the group consisting of halogens, alkyls, hydroxyl, amino, urea, thiol, thio-ether, amino alkyls, carboxylates, metals, metal-containing groups, and derivatives, deuterated forms, or combinations thereof;

wherein R² is selected from the group consisting of halogens, alkyls, hydroxyl, amino, urea, thiol, thio-ether, amino alkyls, carboxylates, metals, metal-containing groups, and derivatives, deuterated forms, or combinations thereof; and wherein X is a crosslinking group, and optionally wherein X is R¹ or R².

9. The optic of claim 1, wherein said carbon-free polymer backbone is crosslinked with sulfur and/or with disulfide (S—S) bonds.

10. The optic of claim 1, wherein said carbon-free polymer backbone is crosslinked with dithiols, $CH_2$, NH, NH(CO)NH, $COO-M^{2+}-OOC$, O(CO)O, or a combination thereof.

11. The optic of claim 1, wherein said carbon-free polymer backbone is crosslinked with $O-Ti(OH)_2-O$.

12. The optic of claim 1, wherein said polymer is a thermoset polymer.

13. The optic of claim 1, wherein said polymer is characterized by a density from about 1.2 g/cm³ to about 1.9 g/cm³.

14. The optic of claim 1, wherein said polymer is characterized by an index of refraction from about 1.3 to about 1.9.

15. The optic of claim 1, wherein said optic includes, or is disposed in physical contact with, an anti-scratch layer, an anti-abrasion layer, an anti-reflection layer, or a combination thereof.

16. The optic of claim 15, wherein said optic includes an anti-scratch layer that contains diamond, diamond-like carbon, sapphire, silicon, ZnS, or a combination thereof.

17. The optic of claim 15, wherein said optic includes an anti-reflection layer in the form of a stack of films that provides anti-reflection properties.

18. The optic of claim 1, wherein said optic includes an anti-rain erosion layer.

19. The optic of claim 18, wherein said anti-rain erosion layer contains an elastomeric material.

20. The optic of claim 19, wherein said elastomeric material is covalently or physically bonded to said optic.

21. The optic of claim 19, wherein said elastomeric material has a storage modulus from about 1 MPa to about 500 MPa, and wherein said elastomeric material has a minimum elongation of 100%.

22. The optic of claim 19, wherein said elastomeric material contains a polyphosphazene-based polymer, a polyphospazene-based copolymer, or a combination thereof.

23. The optic of claim 1, wherein said optic contains toughening filler particles.

24. The optic of claim 23, wherein said toughening filler particles are selected from the group consisting of Ge, $CaF_2$, NaCl, KCl, KBr, diamond, Si, CsI, MgO, $MgF_2$, LiF, NaF, $BaF_2$, ZnS, ZnSe, PbS, Pb Se, $PbF_2$, $LiYF_4$, $NaYF_4$, ThBrI, ThBrCl, and combinations thereof.

25. The optic of claim 23, wherein said toughening filler particles are in the form of spheres, rods, whiskers, platelets, or a combination thereof.

26. The optic of claim 23, wherein said toughening filler particles have an average dimension selected from about 100 nm to about 400 μm.

27. The optic of claim 23, wherein said toughening filler particles have an average dimension that is less than one-half of thickness of said optic.

28. The optic of claim 23, wherein said toughening filler particles have an average volumetric loading from about 1 vol % to about 65 vol % based on volume of said polymer plus volume of said toughening filler particles.

29. The optic of claim 1, wherein said optic includes an anti-fouling layer on an exterior surface of said optic.

30. The optic of claim 29, wherein said anti-fouling layer contains a polyphosphazene-based polymer, a polyphospazene-based copolymer, or a combination thereof.

* * * * *